United States Patent [19]
Hessel

[11] Patent Number: 5,190,556
[45] Date of Patent: Mar. 2, 1993

[54] CORD CUTTER SAMPLER

[75] Inventor: Stephen R. Hessel, Fountain Valley, Calif.

[73] Assignee: O.B. Tech, Inc., Costa Mesa, Calif.

[21] Appl. No.: 672,535

[22] Filed: Mar. 19, 1991

[51] Int. Cl.⁵ .............................................. A61B 17/00
[52] U.S. Cl. ........................................ 606/120; 604/4; 128/760; 128/764
[58] Field of Search ............... 606/120; 604/4, 5, 6, 604/22, 35; 128/760, 764, 765

[56] References Cited

U.S. PATENT DOCUMENTS

| | | | |
|---|---|---|---|
| 3,807,406 | 4/1974 | Rafferty et al. | 604/22 X |
| 4,327,746 | 5/1982 | Feaster | 128/764 |
| 4,428,374 | 1/1984 | Auburn | 606/120 X |
| 4,716,886 | 1/1988 | Schulman et al. | 606/120 |
| 4,781,188 | 11/1988 | Collins | 606/120 |
| 4,938,215 | 7/1990 | Schulman et al. | 606/120 |
| 4,972,843 | 11/1990 | Broden | 128/764 X |
| 4,976,271 | 12/1990 | Blair | 128/764 |
| 5,009,657 | 4/1991 | Cotey et al. | 606/120 |

*Primary Examiner*—Peter A. Aschenbrenner
*Attorney, Agent, or Firm*—Lyon & Lyon

[57] ABSTRACT

There is disclosed herein a device and method for clamping and cutting an umbilical cord so as to enable blood samples to be collected. Clamps are provided as either part of the device or separate therefrom to clamp off a section of the umbilical cord for the cutting and sampling process. The device includes a housing which accommodates vials for receiving the blood samples.

11 Claims, 5 Drawing Sheets

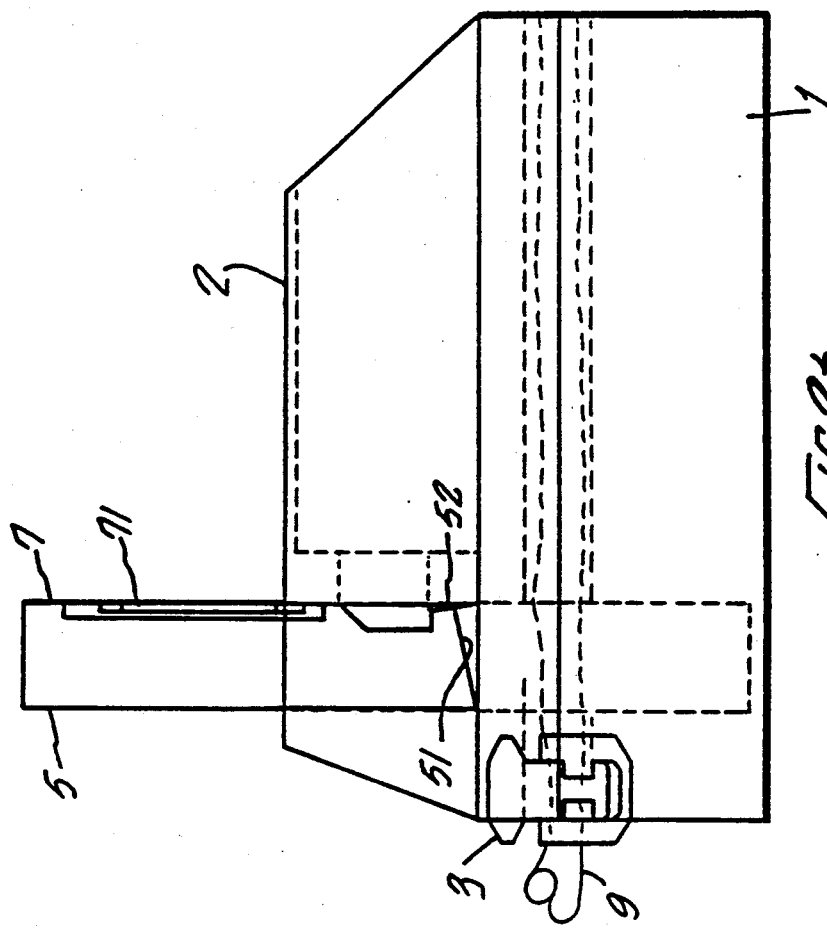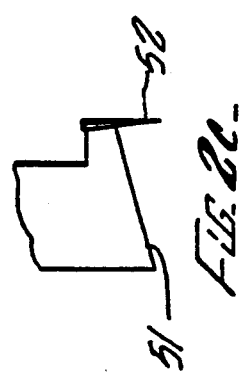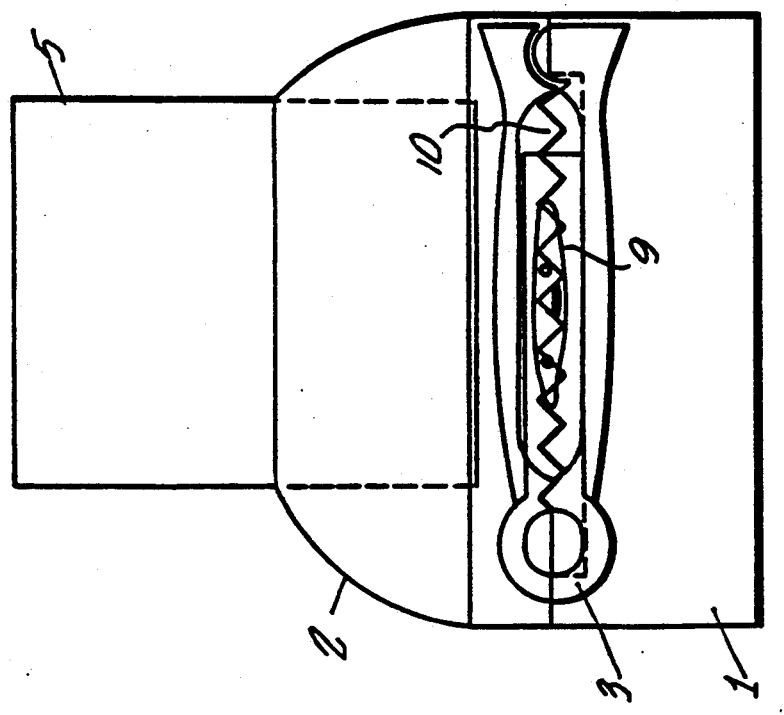

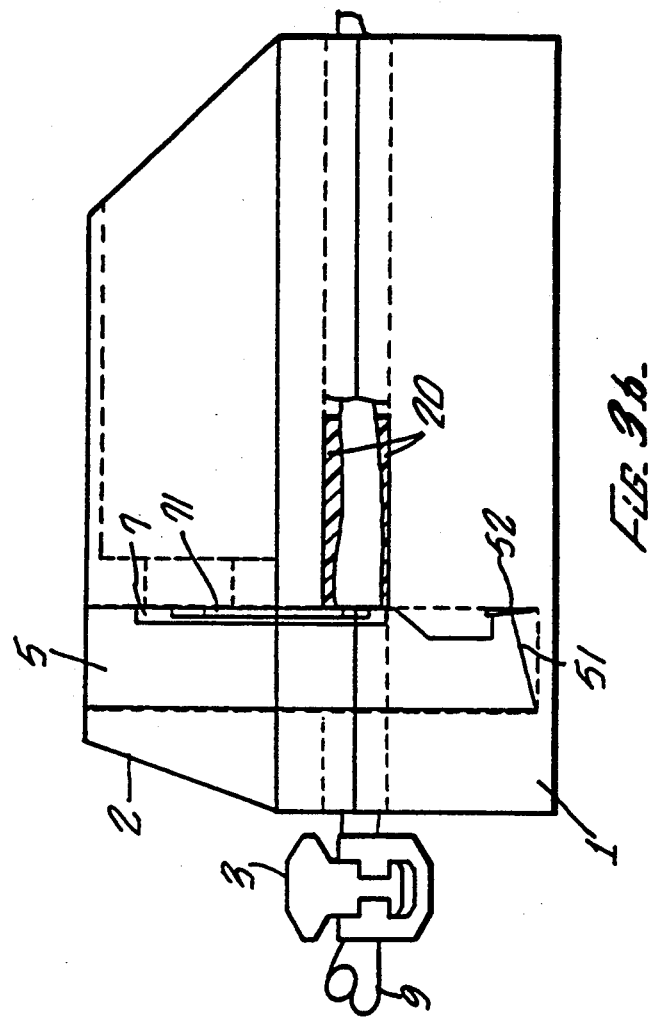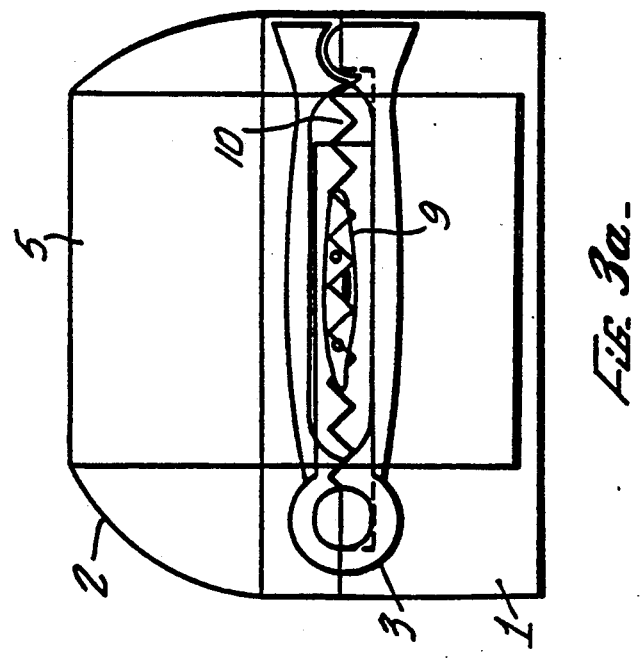

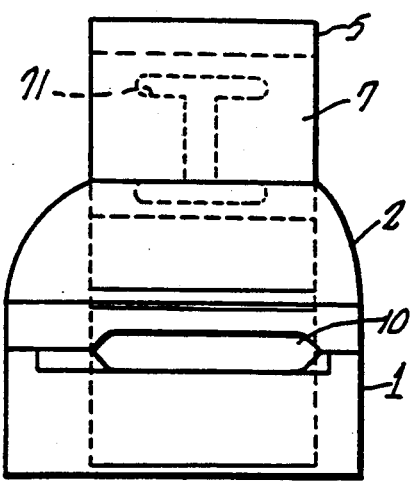
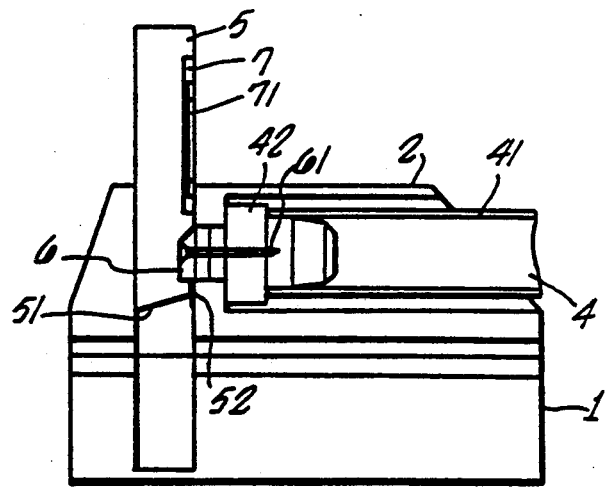
Fig. 4a.  Fig. 4b.
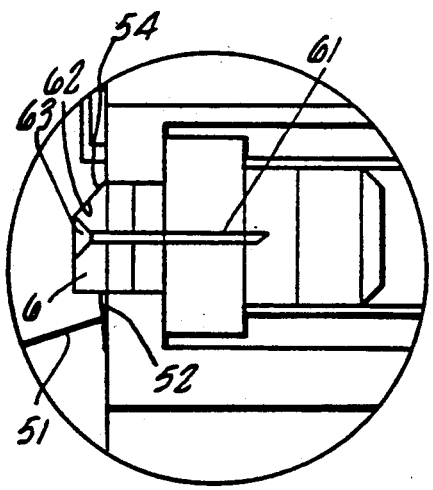
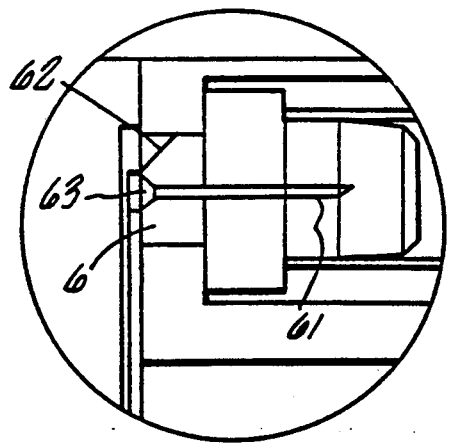
Fig. 4c.  Fig. 4d.
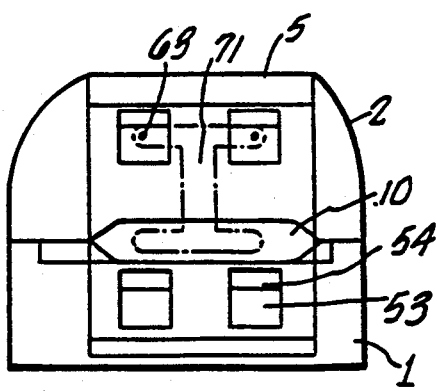
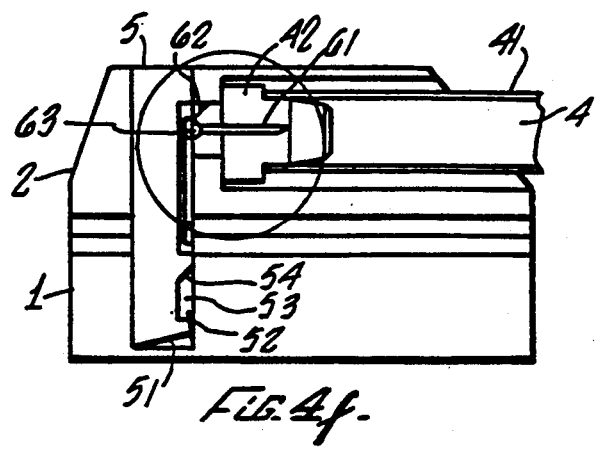
Fig. 4e.  Fig. 4f.

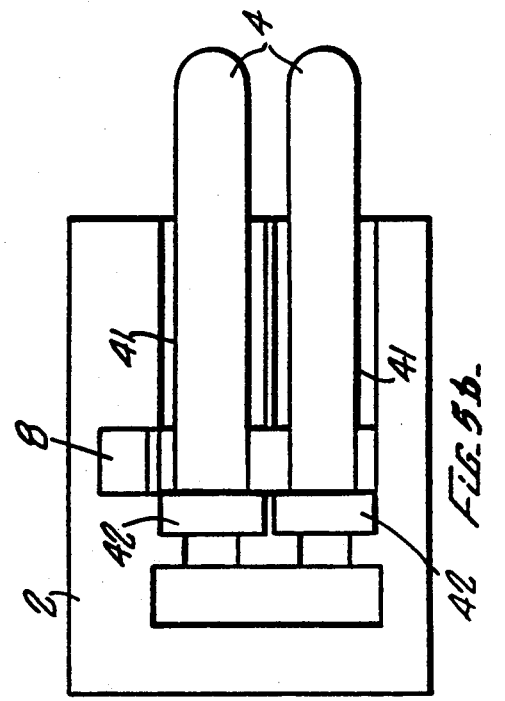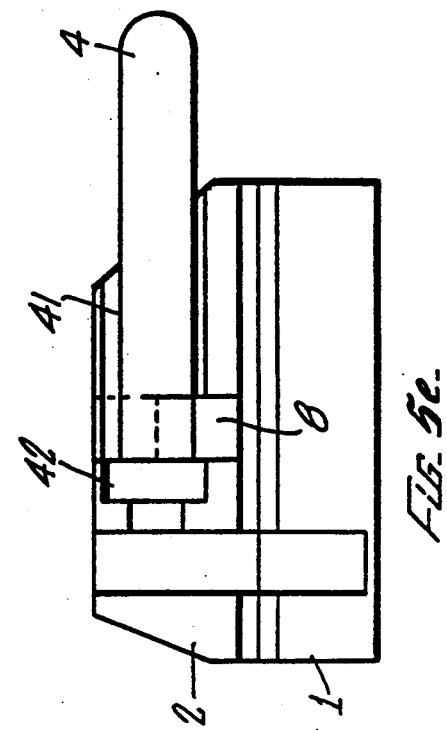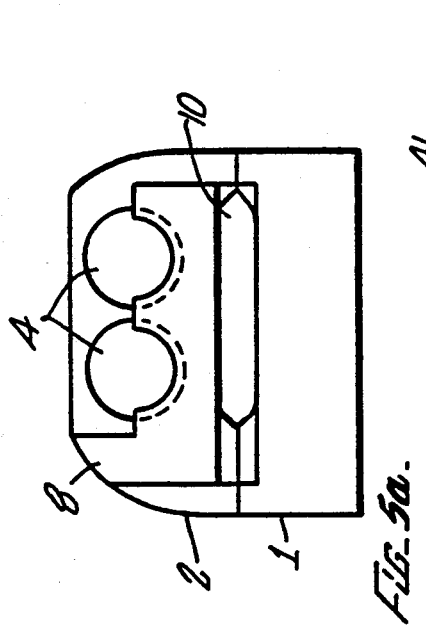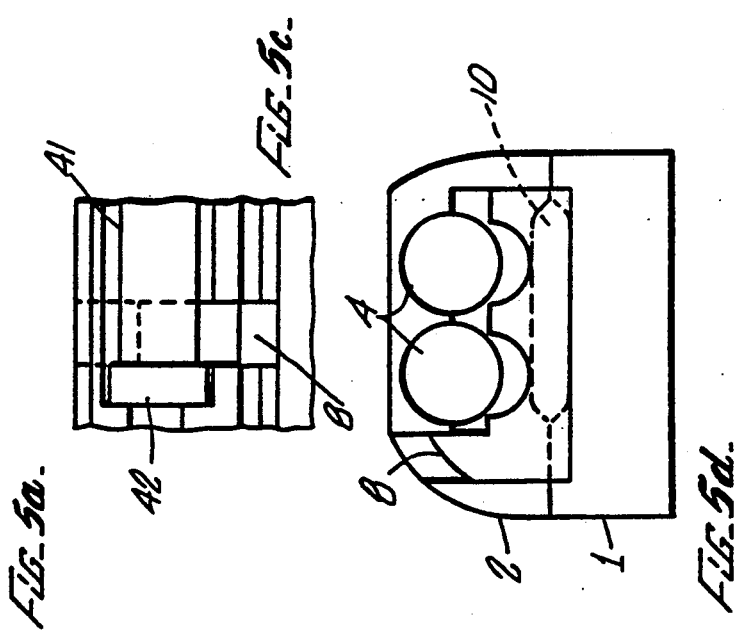

CORD CUTTER SAMPLER

This invention relates to the field of obstetrics and more particularly to an improved apparatus and method for cutting and collecting blood from an umbilical cord.

BACKGROUND OF THE INVENTION

The current process in the delivery of babies requires that the umbilical cord is cut shortly after the moment of birth. The function of the cord is the transmission, between mother and baby, of nutrients and oxygen through the blood flowing in the cord. The cord is thus engorged with blood at birth when severed by the obstetrician to free the baby from the mother. Samples of the blood in the cord are commonly collected at birth for chemical and biological assay to determine if the newborn is subject to possible genetically transmitted diseases.

Currently, the procedure calls for the placement of a small clamp close to the newborn to stop the flow of blood in the cord. At the moment of birth there is a great deal of fluid present, including blood and amniotic fluid from the mother, making the physician's gloved hands slippery. The combination of the small clamp size and the fluid on the gloves creates difficulty in applying the clamp. A second, typically reusable, metal clamp is then applied a short distance from the small clamp toward the mother creating a segregated pocket for cutting. A scissors cut is then made in the center of the pocket by the physician to separate the baby. This formed pocket is under high pressure created by the placement of the two clamps and, upon cutting, the trapped blood within spurts, spraying the general area to as much as ten feet away. Because of the possibility of blood carried diseases this spurting endangers medical personnel. After the baby is removed from the area an attempt is made to obtain a specimen of blood from the section of cord attached to the placenta.

Common practices to obtain this blood include the draining of the cord segment directly into an open vial or direct extraction from the cord by syringe and needle. The draining method requires one person to hold an open ended sample vial below the cord opening while a second person opens the metal clamp and attempts to direct the blood flow into the opening. In most cases the cord segment must be hand "milked" by squeezing the segment toward the vial, probably causing many contaminants to flow into the vial including mother's vaginal blood, amniotic fluids and Wharton's gel which may affect the blood testing. When a syringe and needle is used to extract the blood directly from the cord, care must be taken to prevent inadvertent needle sticks. The contents from the syringe must then be transferred into appropriate vials requiring further manipulation of needles and syringes along with the associated risk. Either blood collection method leaves contamination from blood on the external portions of the vials making it difficult to apply or retrieve patient labels.

SUMMARY OF THE INVENTION

The present invention involves a device and method which provide a much improved method of performing the above described procedure. This device and method accomplish the above procedure in a simple and convenient manner, causing little or no exposure of the medical personnel to inadvertent blood splash, and present clean and adequate samples of cord blood to the physician.

According to an exemplary embodiment of the invention, a device comprises a holding mechanism having pre-attached blood collection vials which fits over an umbilical cord, an umbilical clamp which separates from the housing and remains attached to the infant, a hidden moveable blade which severs the cord through secondary action, means for connecting the open cut blood vessels directly into the blood collection vials, and a secondary clamp to preclude spillage of the cut segment upon removal of the vials. The umbilical clamp and secondary clamp may be separate from the device itself. Because of the simple construction of the device and its use of existing components to collect the blood, it can be manufactured for very low costs and can therefore be disposed after use, precluding the possibility of transmitting diseases to other personnel.

Accordingly, it is a principal object of the present invention to provide a new form of device for cutting and sampling blood from an umbilical cord.

Another object of the present invention is to provide a new method for cutting and sampling blood from an umbilical cord.

These and other objects and features of the present invention will become better understood through a consideration of the following description, taken in conjunction with the drawings in which:

DESCRIPTION OF THE DRAWINGS

FIGS. 2(a-c) are a front view on the left side and a side view on the right of the device in a closed position;

FIGS. 3(a and b) are a front view on the left and side view on the right of the device in a cut position;

FIGS. 4(a-f) comprise detailed views illustrating the cam action of the present device; and FIGS. 5(a-e) comprise detailed views illustrating button action of the device.

DETAILED DESCRIPTION

Figure 1:
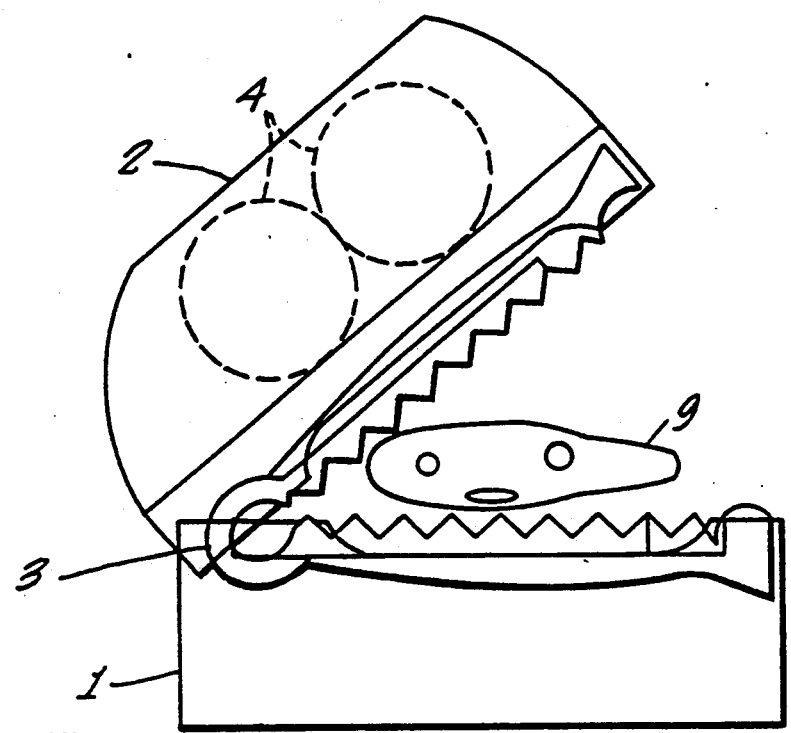
FIG. 1 is a front view of a device constructed in accordance with the present invention in an open position.
Figure 1A:
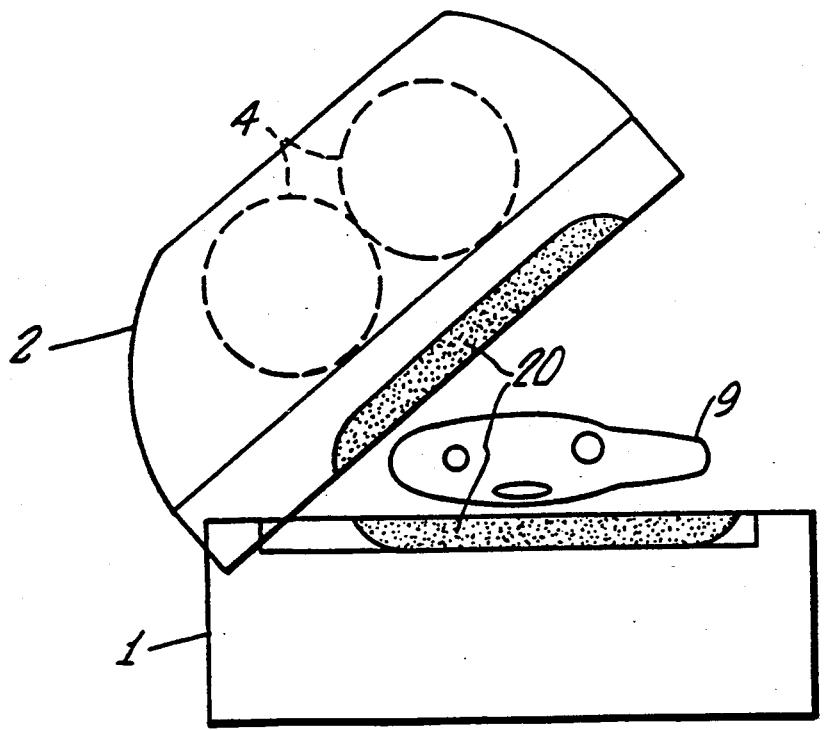
FIG. 1a is a similar front view with an umbilical cord clamp removed from the device.

An embodiment of the present invention is shown in the attached drawings. This embodiment comprises two housings; a bottom housing 1 and a top housing 2 hinged about a common pivot point and having an elongated opening suitable for placement around an exposed umbilical cord. The proximal end of the housing mechanism contains an opened plastic clamp 3 used to permanently clamp the cord near the newborn baby. The most common clamp used today is depicted in the drawing (manufactured by Hollister). Placing the open housing assembly over the cord and closing the unit over the cord will permanently lock the umbilical clamp in place.

A sliding blade 5, is now positioned directly behind the clamp and over the now entrapped section of clamp 3. Movement of the blade 5 in a downward direction will first squeeze the blood in the cord directly next to the clamp 3 back toward the housing by means of the slanted surface 51 before the cutting blade 52 severs the cord thus greatly reducing the blood available for spurting. The cut itself occurs in a closed chamber formed by the housings 1 & 2 and the blade 5, thus protecting the external area from blood during the cutting process.

The inner surfaces of the housings 1 & 2 are coated with suitable amounts of a easily formable gel 20 which makes suitable seals with both the housing surfaces and the cord tissue. Upon the closing of the housings around the cord this gel 20 forms into the interstitial spaces between the housings and the human cord thereby creating an airtight seal. The gel 20 protrudes into the chamber 53 beneath the blade 5 so the severing action creates a flat cross section of cord surrounded by the gel 20 in an air tight formation. Common dentifrice adhesive has worked exceedingly well in this application.

The rear surface of the blade 5 is covered with a soft rubber gasket 7 which has an internal depression 71 shaped to match the inner surfaces of the closed housing. When the blade 5 is positioned in its down location, an elongated slot in the depression mates with the oval openings in the housing allowing blood from the severed vessels to spill into this depression.

Attached to the top housing 2 are two blood vials 4 held in place by a common yoke 8. These containers comprise a glass test tube 41 capped by a thick rubber plug 42. Two vials are needed since one of the vials will contain an anticoagulant. Both coagulated and non coagulated blood are required for the testing. The vials depicted in the illustration are common to the industry and are typically sold with an internal vacuum within the tube 41 such that upon penetration of a needle the vacuum will pull fluid into the tube automatically.

Placed only partially within the rubber plug 42 are needles 61 directly coupled to needle blocks 6 formed of a solid material with an inclined cam surface 62 and having a through hole 63 in direct communication with the needle bore. The blocks 6 are initially located in cavities 53 built into the blade 5. The cavities have a reverse cam surface 54 making direct contact with the cam surface 62. Downward movement of the blade 5 causes the blocks 6 to be pushed forward causing the needles 61 to penetrate through the plugs 42 into the vials making direct communication with the vacuum in the tubes 41. When the blade 5 is positioned in its down location, a second elongated slot in the depression in the gasket 7 mates with the openings in the blocks 6 making communication directly to the severed vessels through the first slot in the depression.

When the blade 5 severs the cord a pulling movement away from the newborn will release the umbilical clamp 3 from the housing assembly as well as a short cord stub. The portion of the cord attached to the placenta will have the clamped assembly anchored onto its end along with the vials 4. Methods of anchoring could be the gel 20 by itself, hook and loop fasteners like that sold under the trademark Velcro glued to the inner housing surfaces and/or localized projections within the formed cord area. In any case the removal of the vials 4 from the housing would result in the now exposed and communicated needles 61 dripping blood which is not acceptable. To preclude this exposure a button 8 attached to the yoke must be activated in a downward direction to move the yoke away from the vials 4 allowing their release. The bottom surface of the button/yoke 8 will move with this downward motion and clamp the trapped cord between its surface and the inner surface of the bottom housing 1 thus preventing any further bleeding.

It can be seen that this device presents a much improved and safer method of clamping and cutting the umbilical cord than is currently available. The device also presents dual samples of cord blood without additional procedures. Because of the compactness and packaging of the device it can be seen that protective coverings can easily be manufactured to protect even the external surfaces of the vials 4.

While an embodiment of the present invention has been shown and described, various modifications may be made without departing from the scope of the present invention, and all such modifications and equivalents are intended to be covered.

What is claimed is:

1. Apparatus for cutting an umbilical cord and collecting a blood sample therefrom comprising
   housing means for receiving and entrapping a section of umbilical cord,
   cutting means for cutting an entrapped section of the cord and sealing at least one cut end of said cord, and
   said housing means comprising means for holding and connecting vial means to provide fluid communication between the vial means and the end of the cord sealed by the cutting means thereby enabling the vial means to receive blood from the umbilical cord.

2. Apparatus as in claim 1 further including first and second clamp means for clamping ends of the section of umbilical cord.

3. Apparatus as in claim 1 further including clamp means for clamping at least one end of the section of umbilical cord.

4. Apparatus for cutting an umbilical cord and collecting a blood sample therefrom comprising
   a housing for receiving and entrapping a section of umbilical cord,
   a cutter for cutting an entrapped section of the cord and securely holding and sealing at least one cut end of said cord, and
   said housing providing sealed fluid communication between the cut end of the cord and a blood receiver thereby enabling the blood receiver to receive blood from the cut end of the umbilical cord.

5. Apparatus as in claim 4 further including clamp means for clamping at least one end of the umbilical cord.

6. An umbilical cord clamping, cutting and blood sampling device comprising
   a top housing and a bottom housing,
      the top housing and bottom housing each having front, back, top, and bottom sides,
      the back side of the top housing and back side of the bottom housing being hingedly connected such that the top and bottom housings may be moved from an open position to a closed position,
      the open position allowing an umbilical cord to be inserted between the top housing and the bottom housing,
      the closed position enabling holding of at least a portion of an umbilical cord,
   a gel disposed on the bottom side of the top housing and the top side of the bottom housing,
   a clamp releasably connected to the bottom side of the top housing and the top side of the bottom housing,
      the clamp having a top arm and a bottom arm,
      the top arm and bottom arm having front, back, top, and bottom sides, the back side of the top arm and back side of the bottom arm being hingedly attached to each other, the front side of the top arm and the front side of the bottom arm having a mating clamp latch, a blade having a cutting edge movably connected to the top housing such that when the top and bottom housings are in a closed position for holding an umbilical cord, the blade may move such that the cutting edge moves in a downward direction from a position over the umbilical cord thereby cutting through the umbilical cord, and at least one vacuum blood collection vial adapted to be connected to the top housing, the vacuum blood collection vial being sealed for holding a vacuum therein, the vacuum blood collection vial being positioned such that when the top and bottom housings are in a closed position holding an umbilical cord and the blade is moved to cut through the umbilical cord, the vacuum of the vacuum blood collection vial is in direct communication with a cut surface of the umbilical cord.

7. An umbilical cord clamping, cutting and blood sampling device comprising a first housing and a second housing, the first housing and second housing each having front, back, top, and bottom sides, the first housing and the second housing being connected such that the first and second housings may be moved from an open position to a closed position, the open position allowing an umbilical cord to be inserted between the first housing and the second housing, the closed position enabling holding of at least a portion of an umbilical cord, a gel disposed on the bottom side of the first housing and the top side of the second housing, a clamp releasably connected to the bottom side of the first housing and the top side of the second housing, the clamp having a top arm and a bottom arm, the top arm and bottom arm having front, back, top, and bottom sides, the back side of the top arm and back side of the bottom arm being hingedly attached to each other, the front side of the top arm and the front side of the bottom arm having a mating clamp latch, a blade having a cutting edge movably connected to the first housing such that when the first and second housings are in a closed position for holding an umbilical cord, the blade may move such that the cutting edge moves in a downward direction from a position over the umbilical cord thereby cutting through the umbilical cord, and at least one vacuum blood collection vial adapted to be connected to the first housing, the vacuum blood collection vial being sealed for holding a vacuum therein, the vacuum blood collection vial being positioned such that when the first and second housings are in a closed position holding an umbilical cord and the blade is moved to cut through the umbilical cord, the vacuum of the vacuum blood collection vial is in direct communication with a cut surface of the umbilical cord.

8. An apparatus for cutting an umbilical cord and collecting blood therefrom in a relatively clean manner comprising a first housing and a second housing, the first housing and second housing each having front, back, top, and bottom sides, the first housing and the second housing being connected such that the first and second housings may be moved from an open position to a closed position, the open position allowing an umbilical cord to be inserted between the first housing and the second housing, the closed position enabling holding of at least a portion of an umbilical cord, a first gel and a second gel, the first gel disposed on the bottom side of the first housing and the second gel disposed on the top side of the second housing such that when the first and second housings are placed in the closed position around an umbilical cord the first and second gels thereby circumscribe the cord forming a seal around the cord and between the cord and the first and second housings without occluding blood flow through the umbilical cord, a blade having a cutting edge movably connected to the first housing such that when the first and second housings are in a closed position for holding an umbilical cord, the blade may move such that the cutting edge moves in a downward direction from a position over the umbilical cord thereby cutting through the umbilical cord and creating an orifice providing direct communication with blood in the umbilical cord, and at least one blood collecting container adapted to be connected to one of the first housing and second housing such that when the first and second housings are in a closed position and the first and second gels form a seal around the umbilical cord and the blade is moved to cut through the umbilical cord thereby creating an orifice, the blood collecting container is in direct liquid communication with the blood in the cord through the orifice such that the blood may be collected in a clean manner.

9. Apparatus for providing a seal around an umbilical cord comprising a first housing and second housing, the first housing and second housing each having front, back, top, and bottom sides, the first housing and the second housing being connected such that the first and second housings may be moved from an open position to a closed position, the open position allowing an umbilical cord to be inserted between the first housing and the second housing, the closed position enabling holding of at least a portion of an umbilical cord, a first gel and a second gel, the first gel disposed on the bottom side of the first housing and the second gel disposed on the top side of the second housing such that when the first and second housings are placed in the closed position around an umbilical cord the first and second gels thereby circumscribe the cord forming a seal around the cord and between the cord and the first and second housings.

10. Apparatus as in claim 9 wherein the first gel and second gel being disposed on the first housing and the second housing to form a seal around the cord and between the cord and the first and second housings without occluding blood flow through the umbilical cord.

11. Apparatus for cutting an umbilical cord and collecting a blood sample therefrom comprising a housing for receiving and entrapping a section of umbilical cord, a cutter for cutting an entrapped section of umbilical cord and directing blood contained within the umbilical cord to a blood receiver, said housing holding said blood receiver and providing fluid communication between the blood within the umbilical cord and the blood receiver thereby enabling the blood receiver to receive blood contained in the umbilical cord in a clean manner.

* * * * *